(12) United States Patent
Buchholz et al.

(10) Patent No.: US 6,515,180 B1
(45) Date of Patent: *Feb. 4, 2003

(54) METHOD FOR THE CATALYTIC, SYMMETRIC DISUBSTITUTION OF CARBOXYLIC ACID AMIDES WITH GRIGNARD REAGENTS

(75) Inventors: Herwig Buchholz, Frankfurt (DE); Urs Welz-Biermann, Mannheim (DE); Armin Meijere, Göttingen (DE)

(73) Assignee: Merck Patent Gesellschaft, Darmstadt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/719,815

(22) PCT Filed: Jun. 18, 1999

(86) PCT No.: PCT/EP99/04254

§ 371 (c)(1),
(2), (4) Date: Mar. 7, 2001

(87) PCT Pub. No.: WO99/65862

PCT Pub. Date: Dec. 23, 1999

(30) Foreign Application Priority Data

Jun. 18, 1998 (DE) .......................................... 198 27 161

(51) Int. Cl.$^7$ ............................................. C07C 211/01
(52) U.S. Cl. ...................... 564/374; 564/373; 564/391; 556/12; 556/95
(58) Field of Search ................................ 564/373, 374, 564/391; 556/12, 95

(56) References Cited

U.S. PATENT DOCUMENTS 4,020,059 A  4/1977  Isamu et al.

FOREIGN PATENT DOCUMENTS

| DE | 2725245 | 12/1977 |
| DE | 2657476 | 6/1978 |
| GB | 921943 | 3/1963 |

OTHER PUBLICATIONS

"Houben–Weyl, Methoden Der Organischen Chemie, vol. XI/1, S. 820–823" 1957, Georg Thieme Verlag, Stuttgart, DE XP002117680 Seite 820, Absatz 2 –Seite 823, Absatz 1.

Beilsteins Handbuch Der Organischen Chemie, vierte Auflage, drittes und viertes Ergaenzungswerk, Bd 20, erster Teil, S. 316 1977, Springer–Verlag, Berlin. Heidelberg. New York XP002117681 Seite 316, Absatz 3.

Kuffner F. Et Al.: "Ueber hochverzweigte aliphatische Verbindungen" Monatshefte FUeR Chemie, Bd. 93, 1962, Seiten 496–475, XP002117676 in der Anmeldung erwaehnt.

Manfred T. Reetz Et al.: "Stereoselective addition of organotitanium reagents to carbonyl compounds" Chemische Berichte., Bd. 118, Nr. 4, 1985, Seiten 1441–1453, XP002117771 Verlag Chemie GMBH. Weinheim., DE ISSN: 0009–2940.

Manfred T. Reetz Et Al.: "Chemoselective addition of organotitanium reagents to carbonyl compounds" Chemische Berichte., Bd. 118, Nr. 4, 1985, Seiten 1421–1440, XP002117770 Verlag Chemie GMBH. Weinheim., DE ISSN: 0009–2940.

Vladimir Chaplinski Et Al.: "Eine nuetzliche Synthese von Cyclopropylaminen aus Carbonsaeurediakylamiden" Angewandte Chemie., Bd. 108, Nr. 4, 1996, Seiten 491–492, XP002117735 VCH Verlagsgesellschaft, Weinheim., DE ISSN: 0044–8249.

Yuying C. Hwang Et Al.: "A synthesis of &–substituted amines" Journal of Organic Chemistry., Bd. 50, Nr. 20, 1985, Seiten 3885–3890, XP002117673 Easton US.

Vladimir Chaplinski Et Al.: "A new versatile reagent for the synthesis of cyclopropylamines . . . " Synlett., 1997, Seiten 111–114, XP002117679 Thieme Verlag, Stuttgart., DE ISSN: 0936–5214.

N. Maxim Et Al.: "Sur la methode de Bouveault . . . " Bulletin De La Societe Chimique De France., Bd. 5, Nr. 3, 1936, Seiten 1084–1093, XP002117677 Paris FR.

Jerry March: "Advanced organic chemistry" 1985, John Wiley, New York. Chischester, Brisbane. Toronto. Singapore XP002117736 Seite 825, Absatz 3.

*Primary Examiner*—Ceila Chang
*Assistant Examiner*—Sonya Wright
(74) *Attorney, Agent, or Firm*—Millen, White, Zelano & Branigan, P.C.

(57) ABSTRACT

The invention relates to a method for symmetrically disubstituting carboxylic acid amides on the geminal carbonyl-C-atom using grignard reagents in the presence of a metal alcoholate compound used as a catalyst and in the presence of another organometalic compound used as a co-catalyst.

10 Claims, No Drawings

METHOD FOR THE CATALYTIC, SYMMETRIC DISUBSTITUTION OF CARBOXYLIC ACID AMIDES WITH GRIGNARD REAGENTS

This application is a 371 of PCT/EP99/04254 filed Jun. 18, 1999.

The present invention relates to a process for disubstituting carboxamides using Grignard reagents in the presence of organometallic compounds as catalyst and a further organometallic compound as cocatalyst.

It is already known from the prior art, in particular from Collect. Czech. Chem. Commun. 1939, 11, 506 and 1959, 24, 110, that the symmetric dialkylation of carboxamides with a Grignard reagent can give amines, the yields of which, however, are not satisfactory.

Accordingly, it was the object of the invention to prepare symmetrically substituted amino compounds with a considerably improved yield by reacting carboxamides with a Grignard reagent.

Using the process according to the invention, it is possible to prepare symmetrically substituted amino compounds with considerably improved yields.

Accordingly, the present invention provides a process for preparing compounds of the general formula (I)

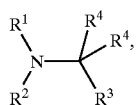

in which $R^1$, $R^2$ and $R^3$ independently of one another are H, A, Ar, $-Si(R^6)_3$, $-Sn(R^6)_3$, $-SR^7$, $-OR^7$, $-NR^8R^9$ or $R^1$ and $R^2$ or $R^1$ and $R^3$ or $R^8$ and $R^9$ can be attached to one another and together form a cyclic ring having 3 to 8 C atoms which optionally contains, in addition to nitrogen, at least one further heteroatom selected from the group consisting of $-S-$, $-O-$ and $-NR^6-$, $R^4$ is A, Ar, $-Si(R^6)_3$, $-Sn(R^6)_3$, $-SR^7$, $-OR^7$, $-NR^8R^9$, in which $R^8$ and $R^9$ are as defined above or $R^8$ and $R^9$ are attached to one another and together form a cyclic ring having 3 to 8 C atoms which optionally contains, in addition to one nitrogen atom, at least one heteroatom selected from the group consisting of $-S-$, $-O-$ and $-NR^6-$; or where two radicals $R^4$ are attached to one another and together form a cyclic ring having 3 to 8 C atoms which optionally contains, in addition to one nitrogen atom, at least one heteroatom selected from the group consisting of $-S-$, $-O-$ and $-NR^6$, with the proviso that $R^4$ in the β position has at most one hydrogen atom, $R^6$, $R^7$, $R^8$ and $R^9$ independently of one another are A or Ar, A is a straight-chain or branched alkyl radical having from 1 to 10 C atoms, a straight-chain or branched alkenyl radical having 2 to 10 C atoms, or a straight-chain or branched alkynyl radical having 2–10 C atoms or a substituted or unsubstituted cycloalkyl radical having 3–8 C atoms, or a mono- or polyunsaturated cycloalkyl radical having 3–8 C atoms, and Ar is a substituted or unsubstituted aryl radical having 6–20 C atoms, characterized in that a compound of the general formula (II)

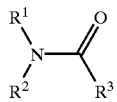

in which $R^1$, $R^2$ and $R^3$ have the meanings given above for the formula (I) is reacted with a nucleophilic reagent of the general formula (IIIa) or a nucleophilic reagent of the general formula (IIIb)

$$Z-R^4 \tag{IIIa}$$

$$Z-R^4-R^4-Z \tag{IIIb}$$

in which $R^4$ has the meaning given for the formula (I), and

Z is Li or MgX where

X is Hal and

Hal is Cl, Br or I.

According to the invention, the process is carried out in the presence of catalytic amounts of a metal alkoxide of the general formula (VI):

$$MX_{4-n}(OR)_n \tag{IV}$$

in which

M is titanium, zirconium or hafnium,

X is Cl, Br, I and

R is alkyl having 1 to 10 C atoms or aryl having 6 to 20 C atoms.

Preference is given to using metal alkoxides in which R is isopropyl. Particular preference is given to using the metal alkoxide $Ti(OiPr)_4$ in which iPr is an isopropyl radical.

The present invention also provides a corresponding process which is carried out in the presence of a cocatalyst. Accordingly, the present invention includes a process which is carried out using metal isopropoxides and alkylsilyl halides as cocatalysts; i.e. metal isopropoxides of the general formula (V) and alkylsilyl halides of the general formula (VI)

$$M'^{(s+)}(O\text{-isopropyl})_s \tag{V}$$

$$R_3SiX \tag{VI}$$

or of the general formula (VII)

$$R_O-(X)_m-Si-Y-(Si)_p-(X)_q-R_O \tag{VII}$$

in which

M' is Al, Ca, Na, R, Si or Mg, preferably Mg or Na, s is an integer from 1 to 4 and is the oxidation stage of the metal, R is alkyl having 1 to 10 C atoms or aryl having 6 to 20 C atoms, X is F, Cl, Br, CN, m is 0, 1, n is 1 to 10, o is 0, 2, 3, p is 0, 1 and q is 0, 1, with the proviso that o=3 and Y≠$(CH_2)_n$ if m=0.

Thus, the invention also provides a process, which is characterized in that a) a carboxamide of the general formula (II), 1–15 mol %, based on the carboxamide, of a metal alkoxide selected from the group consisting of titanium alkoxide, zirconium alkoxide and hafnium alkoxide and, if appropriate, a cocatalyst are initially charged at room temperature under an atmosphere of inert gas in a solvent selected from the group consisting of toluene, THF, n-hexane, benzene and diethyl ether, b) a solution comprising a nucleophilic reagent of the general formula (IIIa) or (IIIb) is added dropwise and c) the mixture is allowed to react with stirring and, after the reaction has ended, worked up in a customary manner, or in that, if Z=MgX, a') magnesium turnings, a carboxamide of the general formula (II), 1–15 mol %, based on the carboxamide, of a metal alkoxide selected from the group consisting of titanium alkoxide, zirconium alkoxide and hafnium alkoxide are initially charged at room temperature under an atmosphere of inert gas in a solvent selected from the group consisting of toluene, THF, n-hexane, benzene and diethyl ether, b') an alkyl halide, dissolved in a solvent selected from the group consisting of toluene, THF, n-hexane, benzene and diethyl ether, and of the general formula (IIIa') or (IIIb')

$$X\text{—}R^4 \quad (IIIa')$$

or $$X\text{—}R^4\text{—}R^4\text{—}X \quad (IIIb')$$

in which $R^4$ and X have the meanings given above, is added dropwise c') the mixture is allowed to react with stirring and, after the reaction has ended, worked up in a customary manner.

Experiments have shown that, using a nucleophilic reagent of the general formula (IIIa) or (IIIb), which may be a Grignard reagent and which may either be generated in situ or added as such to the reaction mixture, it is possible to convert carboxamides of the general formula (II) in the presence of catalytic amounts of titanium alkoxide, zirconium alkoxide or hafnium alkoxide in a simple manner into symmetrically substituted compounds of the general formula (I).

According to the invention, using the process described herein, it is possible to convert, with good yields, carboxamides of the general formula (II) in which $R^1$, $R^2$ and $R^3$ independently of one another can have the following meanings:

H or

A i.e. branched or unbranched alkyl having 1–10 C atoms, such as methyl, ethyl, n- or isopropyl, n-, sec- or t-butyl, pentyl, hexyl, heptyl, octyl, nonyl, decyl and suitable isomers thereof, or cycloalkyl having 3–8 C atoms, such as cyclopropyl, cyclobutyl, cyclopentyl, cyclohexyl, cycloheptyl, cyclooctyl, and corresponding methyl- or ethyl-substituted cycloalkyl groups, or mono- or polyunsaturated cycloalkyl groups, such as cyclopentenyl or cyclopentadienyl, or branched or unbranched alkenyl having 2 to 10 C atoms, such as allyl, vinyl, isopropenyl, propenyl, or branched or unbranched alkynyl having 2 to 10 C atoms, such as ethynyl, propynyl, or aryl having 6 to 20 C atoms which is either unsubstituted or mono- or polysubstituted, such as phenyl, naphthyl, anthryl, phenanthryl, mono- or polysubstituted by substituents selected from the group consisting of $NO_2$, F, Cl, Br, $NH_2$, NHA, $NA_2$, OH and OA, where A can have the meanings given above, can be mono-, poly-, or fully halogenated, preferably fluorinated, or aralkenyl or aralkynyl, where the aryl, alkenyl and alkynyl groups can in each case have the given meanings, such as, for example, in phenylethynyl.

Good yields are in particular also obtained using carboxamides in which $R^1$ and $R^2$ or $R^1$ and $R^3$ together form a cyclic ring having 3–8 C atoms which, in addition to nitrogen, contains further heteroatoms, such as —S—, —O— or —$NR^6$—. Particular preference is given here to compounds in which $R^1$ and $R^2$ or $R^1$ and $R^3$ form a simple cyclic ring which includes the nitrogen of the carboxamide or in which $R^1$ and $R^2$ or $R^1$ and $R^3$ form a cyclic ring which contains, as further heteroatom, an oxygen atom.

Thus, high yields are obtained in this manner when the starting materials used are compounds such as, for example,

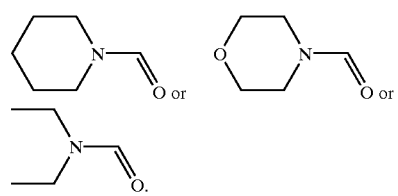

The nucleophilic reagent used can be a Grignard reagent or an organolithium compound of the general formulae (IIIa) or (IIIb), in which the radical $R^4$ is preferably an alkyl radical having 1 to 10 C atoms, such as methyl, ethyl, n- or isopropyl, n-, sec- or t-butyl, pentyl, hexyl, heptyl, octyl, nonyl, decyl and suitable isomers thereof, or cycloalkyl having 3–8 C atoms, such as cyclopropyl, cyclobutyl, cyclopentyl, cyclohexyl, cycloheptyl, cyclooctyl or corresponding methyl- or ethyl-substituted cycloalkyl groups or mono- or polyunsaturated cycloalkyl groups, such as cyclopentenyl or cyclopentadienyl, or branched or unbranched alkenyl having 2 to 10 C atoms, such as allyl, vinyl, isopropenyl, propenyl, or branched or unbranched alkynyl having 2 to 10 C atoms, such as ethynyl, propynyl, or is an aryl radical having 6 to 20 C atoms which is either unsubstituted or mono- or polysubstituted, such as phenyl, napthyl, anthryl, phenanthryl, mono- or polysubstituted bysubstituents selected from the group consisting of $NO_2$, F, Cl, Br, $NH_2$, NHA, $NA_2$, OH and OA, where A can have the meanings given above, can be mono-, poly- or fully halogenated, preferably fluorinated, or is an aralkyl radical having 7 to 20 C atoms, such as benzyl, optionally mono- or polysubstituted by substituents selected from the group consisting of $NO_2$, F, Cl, Br, $NH_2$, NHA, $NA_2$, OH and OA, where A can have the meanings given above, can be mono-, poly- or fully halogenated, preferably fluorinated, is an aralkenyl or aralkynyl radical, where the aryl, alkenyl and alkynyl group can in each case have the given meanings, such as, for example, in phenylethynyl.

Furthermore, the radical $R^4$ in the general formula (IIIa) can be —$Si(R^6)_3$, —$Sn(R^6)_3$, —$SR^7$, —$OR^7$, —$NR^8R^9$, in which $R^6$, $R^7$, $R^8$ and $R^9$ independently of one another can have the abovementioned meanings or $R^8$ and $R^9$ are attached to one another and together form a cyclic ring having 3 to 8 C atoms which may optionally, in addition to a nitrogen atom, contain at least one heteroatom selected from the group consisting of —S—, —O— and —NR$^6$—;

or two radicals R$^4$ in the general formula (IIIb) can be an alkyl having 2–7 C atoms, so that, in the reaction according to the invention, a compound of the general formula (I) is formed in which two radicals R$^4$ form a cyclic ring having 3 to 8 atoms.

Particularly preferably, R$^4$ has the meaning of an alkyl radical, such as, for example, methyl, ethyl, n- or isopropyl, n-, sec- or t-butyl, pentyl, hexyl, or of a cycloalkyl radical, such as, for example, cyclopropyl, cyclobutyl, cyclopentyl, cyclohexyl, or of an aryl radical, such as, for example, phenyl, or of an aralkyl radical, such as, for example, benzyl.

The radical Z in the general formulae (IIIa) and (IIIb) preferably represents a radical MgX where X is Cl or Br, or the radical Z is lithium.

Particular preference according to the invention is given to using Grignard compounds such as: methylmagnesium bromide, ethylmagnesium bromide, n- or isopropylmagnesium bromide, iso-, sec- or tert-butylmagnesium bromide, n-hexylmagnesium bromide, cyclohexylmagnesium chloride, allylmagnesium bromide, vinylmagnesium bromide, cyclonentylmagnesium bromide, cyclopentylmagnesium chloride, phenylmagnesium bromide, benzylmagnesium chloride, for the reaction.

Thus, the present invention also provides the compounds, prepared by the process according to the invention, of the general formula (I) in which the radicals R$^1$ to R$^4$ have the meanings given above.

Furthermore, it was found that only if a cocatalyst is added, the geminal symmetric dialkylation reactions according to the invention start even at room temperature and result in the complete conversion of the starting materials in a relatively short reaction time.

Suitable cocatalysts for this reaction are metal isopropoxides and alkylsilyl halides. Particularly suitable are metal isopropoxides of the general formula (V) and alkylsilyl halides of the general formula (VI)

M'$^{(s+)}$(O-isopropyl)$_s$     (V)

R$_3$SiX     (VI)

or of the general formula (VII)

R$_0$—(X)$_m$—Si—Y—(Si)$_p$—(X)$_q$—R$_0$     (VII)

in which

M' is Al, Ca, Na, K, Si or Mg, preferably Mg or Na, s is an integer from 1 to 4 and is the oxidation stage of the metal, R is alkyl having 1 to 10 C atoms or aryl having 6 to 20 C atoms, X is F, Cl, Br, CN, m is 0, 1, n is 1 to 10, o is 0, 2, 3, p is 0, 1 and q is 0, 1, with the proviso that o=3 and Y≠(CH$_2$)$_n$ if m=0.

Preference is given to using metal isopropoxides in which s is an integer from 1 to 4 and is the oxidation stage of the metal and M' is Al, Ca, Na, K, Si or Mg. Particular preference is given to Mg or Na.

Preference is given to using alkylsilyl halides in which R is alkyl having 1 to 6 C atoms. Particular preference is given to those in which R is alkyl having 1 to 3 C atoms and X is chlorine.

Particularly suitable cocatalysts are, inter alia, the following silicon compounds:

(CH$_3$)$_3$SiCl (CH$_3$)$_2$ClSi(CH$_2$)$_2$SiCl(CH$_3$)$_2$ (CH$_3$)$_2$ClSi(CH$_2$)$_3$CN

[(CH$_3$)$_3$Si]$_2$O

[(CH$_3$)$_3$Si]$_2$NH and

[(CH$_3$)$_3$Si]$_2$.

It has been found that the addition of from 0.7 to 1.2 mol, in particular from 0.9 and 1.1 mol, of a cocatalyst based on one mol of starting material leads to improved results such as, for example, higher yields, lower reaction temperature or shorter reaction times.

As can be demonstrated using examples, under favourable conditions a complete conversion of the carboxamide according to the general equation (Eq. 1) has taken place after just one hour:

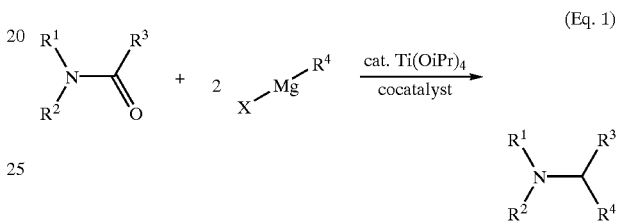

(Eq. 1)

For carrying out the process according to the invention, the catalyst used can be a commercial metal alkoxide selected from the group consisting of titanium alkoxide, zirconium alkoxide and hafnium alkoxide. Preference is given to using titanium tetraisopropoxide. The metal alkoxide, preferably titanium tetraisopropoxide, is used as a solution in a suitable solvent, which is dried beforehand. Suitable solvents are, for example aliphatic or aromatic hydrocarbons or ethers. Preference is given to using solvents selected from the group consisting of toluene, THF, n-hexane, benzene and diethyl ether, which are dried prior to the reaction by methods known to the person skilled in the art. Drying can be carried out with the aid of magnesium sulphate, calcium chloride, sodium, potassium hydroxide or by other methods.

A preferred embodiment of the process according to the invention comprises initially charging the titanium tetraisopropoxide used as catalyst in an amount of from 1 to 15, preferably 1.5 to 14, in particular 2 to 10 and very particularly preferably from 3 to 6 mol %, based on one mol of the amide used as starting material, in the form of a solution adjusted to a temperature of from 10 to 30° C., preferably 15–25° C., particularly preferably to a temperature of about 20° C. Under an atmosphere of inert gas (nitrogen or argon), the starting material, either as such in liquid form or dissolved in a solvent selected from the group consisting of toluene, THF, n-hexane, benzene and diethyl ether, is slowly added dropwise with stirring. An amount of cocatalyst which corresponds to the amount to be reacted is then added dropwise, if required likewise in a solvent. The reaction mixture obtained is stirred for a short period, i.e. for a few minutes, at a constant temperature. Such an excess of the nucleophilic reagent of the general formula (IIIa) or (IIIb), in particular a Grignard reagent, is then slowly added to the resulting reaction mixture that substitution of the geminal carbonyl C atom by two identical substituents, i.e. a symmetric substitution of the geminal carbonyl C atom, can take place. The addition of a nucleophilic reagent according to the invention prepared by methods generally known to the person skilled in the art should take place at such a rate that the temperature of the reaction mixture does not exceed 50° C. It is advantageous to carry out the addition of the nucleophilic reagent, i.e. of the Grignard reagent or the lithium compound, with efficient mixing, preferably vigorous stirring. To shift the reaction equilibrium to the side of the desired symmetrically substituted product, the nucleophilic reagent used, preferably a Grignard reagent, is added in an amount of from 2.1 to 3 mol per mole of starting material that participates in the reaction. Preference is given to adding the Grignard reagent in an amount of from 2.2 to 2.6 mol, based on 1 mol of starting material. If a nucleophilic reagent or Grignard reagent of the general formula (IIIb) is used, only equimolar amounts, based on the starting material, are added to the reaction solution, corresponding to twice the number of reactive groups.

After the addition of the Grignard reagent has ended, the reaction mixture is stirred for some time at a constant temperature, until the reaction is brought to completion.

Another variant of the process according to the invention comprises preparing the Grignard reagent in situ by reacting magnesium with a compound of the general formula (IIIa') or (IIIb') in which $R^4$ and X have the meanings given above. In the in situ preparation of the Grignard compounds, the amount of magnesium is preferably 2 to 5 times the molar amount, preferably 2.8 to 3.2 times the molar amount, based on the compounds of the general formula (II) used as starting material, and the amount of the compound of the general formula (IIIa') or (IIIb') is 2 to 3.8 times the molar amount, preferably 2.2 to 2.6 times the molar amount, based on the compound of the general formula (II).

If no cocatalyst is added to the reaction mixture, the reaction temperature can, after addition of the nucleophilic reagent has ended and the mixture has been mixed thoroughly, be adjusted to about 80° C., preferably to from 60 to 70° C., in particular to 65° C.

Thus, by the synthesis according to the invention it is possible to prepare symmetrically substituted amino compounds of the general formula (I) with good or satisfactory yields within adequate reaction times. In an advantageous manner, it is possible, by adding one of the catalysts in combination with one of the cocatalyst compounds described of the general formulae (V), (VI) or (VII), to reduce the reaction times considerably, in the most favourable case to one hour, without this resulting in a reduction in the yields obtained.

Thus, the present invention also provides the use of a catalyst system comprising a metal alkoxide selected from the group consisting of titanium alkoxide, zirconium alkoxide and hafnium alkoxide as catalyst and a compound of the general formulae (V), (VI) or (VII) with the meanings given above, and the use of this catalyst system for preparing the symmetrically substituted compounds of the general formula (I).

For example, 5 mmol of starting material are, at 20° C. and under an atmosphere of inert gas, added dropwise with stirring to a solution of 3 mol % of titanium, tetraisopropoxide in 40 ml of dried tetrahydrofuran. 5 mmol of cocatalyst, likewise taken up in dried tetrahydrofuran, are added slowly with stirring to this mixture. The mixture is stirred at 20° C. for 5 minutes, and 12 mmol of Grignard reagent are then added at such a rate that the temperature of the reaction mixture does not exceed 50° C. Stirring is continued for one hour, until the reaction has gone to completion.

After the reaction according to the invention, work-up of the reaction mixture can be carried out in a manner known to the person skilled in the art.

Here, the products can be precipitated as salts using solutions of hydrochloric acid, for example a 1 molar ethereal solution of hydrochloric acid, and be filtered off and, if required, purified by recrystallization.

To remove the Lewis acid, it is possible, for example, to add a suitable amount of saturated ammonium chloride solution and water, followed by further vigorous stirring for a plurality of hours (1–3 hours). The resulting precipitate is separated off and washed with a little ether, preferably diethyl ether. The filtrate is made alkaline (pH>10) by addition of a suitable base, such as an NaOH, KOH, sodium carbonate or potassium carbonate solution, preferably sodium hydroxide solution. The phases that are formed are then separated, and the aqueous phase is extracted repeatedly (for example in the special case given above three times with in each case 30 ml) with diethyl ether. The combined organic phases are washed with (for example 15 ml of) saturated sodium chloride solution and can be dried over potassium carbonate, magnesium sulphate or sodium sulphate and filtered.

The products can be purified by various routes using methods known to the person skilled in the art, such as, for example, in the following manner:

1. They are precipitated as hydrochlorides using 1 M ethereal hydrochloric acid solution and filtered off (the resulting product is, if required, purified by recrystallization).

2. The organic phase is extracted repeatedly with a 0.5 M acid solution, preferably an aqueous hydrochloric acid solution. The extract obtained is adjusted to pH>10 using bases, preferably 2 M aqueous sodium hydroxide solution, and extracted at least once, preferably repeatedly, with diethyl ether. The resulting organic phases, which contain the reaction product, can be dried, if appropriate, over potassium carbonate, magnesium sulphate or sodium sulphate and be freed from the organic solvent under reduced pressure.

3. Furthermore, it is possible to isolate the reaction product by removing the organic solvent under reduced pressure and separating the residue that remains by column chromatography, to isolate the reaction product.

In the general description of the process procedure given above, the Grignard reagents can also be replaced by the corresponding lithium compounds. The corresponding lithium compounds, like the Grignard reagents, can be prepared by methods generally known to the person skilled in the art, and they can be reacted according to the invention in the same manner as described above.

The compounds of the general formula (I) prepared according to the invention can be used, for example, as intermediates in the preparation of sulphur- or selenium-containing amines for the chiral catalysis of diethyl zinc syntheses (literature: Werth, Thomas; Tetrahydron Lett. 36; 1995, 7849–7852, Werth, Thomas et al. Helv. Chim. Acta 79, 1996, 1957–1966).

To illustrate and better understand the present invention, examples are given below. However, owing to the general validity of the described principle of the invention, they are not meant to reduce the scope of the present application to just these examples.

EXAMPLES

Titanium-tetraisopropoxide-induced Symmetric Dialkylation of Carboxamides Using Grignard Reagents According to the reaction shown in Equation 1, the following reactions were carried out using one equivalent of $(CH_3)_3SiCl$ as cocatalyst:

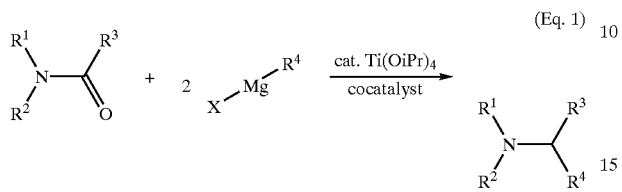

(Eq. 1)

Examples 1 to 4

At 20° C. and under an atmosphere of nitrogen, 5 mmol of the amide listed in Table 1 and 5 mmol of $C(CH_3)_3SiCl_3$ as cocatalyst are added dropwise to a solution of 3 mol % of $Ti(O\text{-isopropyl})_4$, based on the amide given in Table 1, in 40 ml of dry tetrahydrofuran. The mixture is stirred at 20° C. for 5 min. 12 mmol of the Grignard reagent given in Table 1 are then added to the reaction mixture at such a rate that the temperature of the reaction mixture does not exceed 50° C. The mixture is then stirred at the reaction temperature given in Table 1 for the reaction time given in Table 1, until the reaction has ended.

Example 1a

Deviating from this procedure, in Example 1a 15 mmol of magnesium turnings are initially charged in 10 ml of tetrahydrofuran at 20° C., under at atmosphere of nitrogen. 10 mol %, based on the amide given in Table 1, of $Ti(O\text{-isopropyl})_4$ and 5 mmol of the amide given in Table 1, dissolved in tetrahydrofuran, are then added. 12 mmol of phenyl bromide are slowly added dropwise, such that the mixture boils gently. In the reaction time of 1 hour and at a reaction time of 25° C., with prior addition of 5 mmol of the cocatalyst indicated above, the product indicated in Table 1 is obtained in the yield given in Table 1, after 1 hour.

Work-up of the Reaction Products

To remove the Lewis acid, 15 ml of saturated ammonium chloride solution and 15 ml of water are added with vigorous stirring (1 hour). Any precipitate that is formed is filtered off with suction using a Nutsche/suction flask, and the filter residue is washed twice with 20 ml of dry diethyl ether. The filtrate is made alkaline (pH>10) by addition of sodium hydroxide solution. The phases are then separated in a separating funnel. The aqueous phase is extracted three times with in each case 30 ml of diethyl ether. The combined organic phases are washed with saturated sodium chloride solution and the separated organic phase is dried over potassium carbonate and filtered. The solvent is removed using a rotary evaporator. The residue is chromatographed over 20 g of silica gel, using a mixture of heptane/tert-butyl methyl ether 50/1 as mobile phase.

TABLE 1

Ti(OiPr)$_4$-induced reaction of carboxamides with R$_4$MgX.

| Amide | Product | Yield | R$^4$MgX | Reaction conditions |
|---|---|---|---|---|
| | | 84% | PhMgBr | 24 h/60° C./ 3 mol % Ti(OiPr)$_4$ |
| | | 56% | PhBr/Mg | 1 h/RT/10 mol % Ti(OiPr)$_4$ |
| | | 95% | PhMgBr | 1 h/RT/3 mol % Ti(OiPr)$_4$/5 mmol Cocat |
| | | 71% | BnMgCl | 1 h/RT/3 mol % Ti(OiPr)$_4$/5 mmol Cocat |
| | | 70% | BnMgCl | 1 h/RT/3 mol % Ti(OiPr)$_4$/5 mmol Cocat |

What is claimed is:

1. A process for preparing compounds of the formula (I)

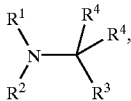  (I)

in which
R$^1$, R$^2$ and R$^3$ independently of one another are H, A, Ar, —Si(R$^6$)$_3$, —Sn(R$^6$)$_3$, —SR$^7$, —OR$^7$, —NR$^8$R$^9$,
R$^4$ is A, Ar, —Si(R$^6$)$_3$, —Sn(R$^6$)$_3$, —SR$^7$, —OR$^7$, —NR$^8$R$^9$, in which R$^8$, R$^9$ and R$^{10}$ are as defined above,
with the proviso that when R$^4$ is A, R$^4$ may not have more than one hydrogen in the β position,
R$^6$, R$^7$, R$^8$ and R$^9$ independently of one another are A or Ar,
A is a straight-chain or branched alkyl radical having from 1 to 10 C atoms, a straight-chain or branched alkenyl radical having 2 to 10 C atoms, or a straight-chain or branched alkynyl radical having 2–10 C atoms or a substituted or unsubstituted cycloalkyl radical having 3–8 C atoms, or a mono- or polyunsaturated cycloalkyl radical having 3–8 C atoms, and
Ar is a substituted or unsubstituted aryl radical having 6–20 C atoms, wherein a compound of the general formula (II)

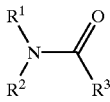  (II)

in which R$^1$, R$^2$ and R$^3$ have the meanings given above for the formula (I) is reacted with a nucleophilic reagent of the general formula (IIIa) or a nucleophilic reagent of the general formula (IIIb)

Z—R$^4$  (IIIa)

Z—R$^4$—R$^4$—Z  (IIIb)

in which
R$^4$ has the meaning given for the formula (I), and
Z is Li or MgX where
X is Hal and
Hal is Cl, Br or I,
wherein the process is carried out in the presence of catalytic amounts of a metal alkoxide selected from the group consisting of titanium alkoxide, zirconium alkoxide and hafnium alkoxide,
and wherein the process is carried out in the presence of a cocatalyst.

2. A process according to claim 1, carried out in the presence of a metal isopropoxide or an alkylsilyl halide cocatalyst.

3. Process according to claim 1, wherein the cocatalyst used is a metal isopropoxide of formula (V) or an alkylsilyl halide of formula (VI)

M$'^{(s+)}$(O-isopropyl)$_s$  (V)

R$_3$SiX  (VI)

in which
M' is Al, Ca, Na, K, Si or Mg, preferably Mg or Na,
s is an integer from 1 to 4 and is the oxidation stage of the metal,
R is alkyl having 1 to 10 C atoms or aryl having 6 to 20 C atoms,
X is F, Cl, Br, CN,
or an alkylsilyl halide of the formula (CH$_3$)$_2$ClSi(CH$_2$)$_2$SiCl(CH$_3$)$_2$, (CH$_3$)$_2$ClSi(CH$_2$)$_3$CN,

[(CH$_3$)$_3$Si]$_2$O,

[(CH$_3$)$_3$Si]$_2$NH or

[(CH$_3$)$_3$Si]$_2$.

4. A process according to claim 1; wherein the catalyst used is a metal alkoxide of the formula (IV)

MX$_{4-n}$(OR)$_n$  (IV)

in which
M is titanium, ziroconium or hafnium,
X is Cl, Br, I and
R is alkyl having 1 to 10 C atoms or aryl having 6 to 20 C atoms,
n is an integer from 1 to 4.

5. A process according to claim 1, further comprising;
a) initially charging a carboxamide of the general formula (II), 1–15 mol %, based on the carboxamide of the metal alkoxide selected from the group consisting of titanium alkoxide, zirconium alkoxide and hafnium alkoxide and optionally the cocatalyst at 10–30° C. under an atmosphere of inert gas in a solvent selected from the group consisting of toluene, THF, n-hexane, benzene and diethyl ether,
b) adding dropwise a solution comprising a nucleophilic reagent of the general formula (IIIa) or (IIIb)
in which
R$^4$ and X have the meanings given in claim 1 and
c) reacting the mixture with stirring,
or in that, if Z=MgX,
a') initially charging magnesium turnings, a carboxamide of the general formula (II), 1–15 mol %, based on the carboxamide of the metal alkoxide selected from the group consisting of titanium alkoxide, zirconium alkoxide and hafnium alkoxide and the cocatalyst at 10–30° C. under an atmosphere of inert gas in a solvent selected from the group consisting of toluene, THF, n-hexane, benzene and diethyl ether,
b') adding dropwise an alkyl halide, dissolved in a solvent selected from the group consisting of toluene, THF, n-hexane, benzene and diethyl ether, and of the general formula (IIIa') or (IIIb')

X—R$^4$  (IIIa')

or

X—R$^4$—R$^4$—X  (IIIb')

in which
R$^4$ has the meanings given in claim 1 and
X has the meanings given in the preceding claims
c') reacting the mixture with stirring.

6. A process according to claim 5, wherein process step a) or a') is carried out at room temperature of from 15 to 25° C.

7. A process according to claim 5, wherein process step a) or a') is carried out at room temperature.

8. A process according to claim 1, wherein the nucleophilic reagent used is a lithium compound of the general formula (IIIa) or (IIIb) in which $R^4$ has the meanings given in claim 1.

9. Process according to claim 1, in that the nucleophilic reagent used is a compound of the general formula (IIIa) or (IIIb) in which $R^4$ is methyl, ethyl, n- or isopropyl, iso-, sec- or tert-butyl, n-hexyl, cyclopentyl, cyclohexyl, allyl, vinyl, phenyl or benzyl.

10. Process according to claim 1, in that the compound that is reacted is a compound of the general formula (II) in which $R^1$, $R^2$ and $R^3$ independently of one another are H, methyl, ethyl, n- or isopropyl, iso-, sec- or tert-butyl, n-hexyl, phenyl or benzyl.

\* \* \* \* \*